US00PP11837P2

(12) United States Plant Patent
Klemmedson

(10) Patent No.: US PP11,837 P2
(45) Date of Patent: Apr. 17, 2001

(54) BEGONIA PLANT NAMED 'DANA'

(75) Inventor: Mark Klemmedson, Redmond, WA (US)

(73) Assignee: Klem's Greenhouse, Inc., Redmond, WA (US)

( * ) Notice: Subject to any disclaimer, the term of this patent is extended or adjusted under 35 U.S.C. 154(b) by 0 days.

(21) Appl. No.: 09/422,170

(22) Filed: Oct. 22, 1999

(51) Int. Cl.[7] ..... A01H 5/00
(52) U.S. Cl. ..... Plt./348

(58) Field of Search ..... Plt./343, 344, 348, Plt./349

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Begonia plant named 'Dana', characterized by its compact, upright, uniform and freely branching plant habit; strong, thick stems; freely flowering habit with about eight flowers per axillary cyme; fully double intense dark pink flowers that are about 6.6 cm in diameter; dark green leaves; and excellent post-production longevity.

1 Drawing Sheet

BACKGROUND OF THE INVENTION

The present invention relates to a new and distinct cultivar of Begonia plant, botanically known as *Begonia×hiemalis,* commercially known as Elatior Begonia, and hereinafter referred to by the name 'Dana'.

The new Begonia was discovered by the Inventor in a controlled environment in Redmond, Wash., in 1996, as a naturally-occurring mutation of *Begonia×hiemalis* 'Barkos', disclosed in U.S. Plant Pat. No. 9,523. The new Begonia was observed as a single plant in a group of flowering plants of the parent cultivar. The selection of this plant was based on its unique flower color.

Asexual reproduction of the new Begonia by terminal cuttings taken in a controlled environment in Redmond, Wash., has shown that the unique features of this new Begonia are stable and reproduced true to type in successive generations.

SUMMARY OF THE INVENTION

The cultivar 'Dana' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dana'. These characteristics in combination distinguish 'Dana' as a new and distinct Begonia:

1. Compact, upright, uniform and freely branching plant habit.
2. Strong, thick stems.
3. Extremely freely flowering with about eight flowers per axillary cyme.
4. Fully double intense dark pink flowers that are about 6.6 cm in diameter.
5. Dark green leaves.
6. Excellent post-production longevity; flowers do not abscise under low light conditions.

In side-by-side comparisons conducted by the Inventor in Redmond, Wash., plants of the new Begonia differ from plants of the parent cultivar 'Barkos' in the following characteristics:

1. Plants of the new Begonia are more freely branching than plants of the cultivar 'Barkos'.
2. Branching occurs faster and more uniformly on plants of the new Begonia compared to plants of the cultivar 'Barkos'.
3. Plants of the new Begonia are more uniform in plant growth than plants of the cultivar 'Barkos'.
4. Flowers of plants of the new Begonia are slightly smaller and have fewer tepals than plants of the cultivar 'Barkos'.
5. Flower color of plants of the new Begonia is dark pink whereas flower color of plants of the cultivar 'Barkos' is red.

BRIEF DESCRIPTION OF THE PHOTOGRAPHS

The accompanying colored photographs illustrate the overall appearance of the new Begonia, showing the colors as true as it is reasonably possible to obtain in colored reproductions of this type.

The photograph at the top of the sheet comprises a side perspective view of a typical flowering plant of 'Dana'.

The photograph at the bottom of the sheet comprises a close-up view of typical flowers of 'Dana'. Flower and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Redmond, Wash., under commercial practice in a fiberglass-covered greenhouse. Average day and night temperatures were about 21° C. and maximum light levels were about 3,000 foot-candles. Plants were flowered under short nyctoperiods of eight to twelve hours. Measurements and numerical values represent averages for typical flowering plants grown in 15-cm containers. Plants were about 10 to 12 weeks old after planting.

Botanical classification: *Begonia×hiemalis* cultivar 'Dana'.

Commercial classification: Elatior Begonia.

Parentage: Naturally-occurring mutation of *Begonia× hiemalis* cultivar 'Barkos', disclosed in U.S. Plant Pat. No. 9,523.

Propagation:

*Type.*—Terminal cuttings.

*Time to initiate roots.*—About 14 days at temperatures about 22° C.

*Time to develop roots.*—About 39 days at temperatures about 22° C.

*Root description.*—Fine, fibrous, and freely branching; plants typically do not form tubers.

Plant description:

*Plant form.*—Compact; upright and somewhat spreading potted plant; uniform growth habit; very early and freely branching, dense and bushy, about three laterals branches per primary stem; good stem and stem base strength. Flowers are fully double and abundant. Plants flower continuously.

*Growth habit.*—Moderate growth rate, vigorous. Suitable for 11 to 15.5-cm containers. Under optimal environmental and cultural conditions, usually about 10 weeks are required to produce finished flowering potted plants from rooted cuttings. Vegetative shoots are formed at basal nodes and flowering shoots are formed at upper nodes.

*Plant height.*—To top of flowers, about 34.5 cm; to top of leaf plane, about 27 cm.

*Plant width.*—About 51 cm.

*Growth rate/vigor.*—Moderate.

*Lateral branches.*—Appearance/aspect: Cylindrical; upright to somewhat outwardly angled. Strength: Very good. Length: About 19 cm. Diameter: About 1 cm. Internode length: About 3.8 cm. Texture: Mostly smooth with sparse small white hairs; fleshy. Color: 144A; lighter green towards apex; some anthocyanin at lower nodes, close to 53A.

*Leaves.*—Arrangement: Simple, alternate. Quantity: Densely foliage, about nine per lateral branch. Length: About 10.2 cm. Width: About 14.5 cm. Shape: Asymmetrical, roughly reniform. Apex: Somewhat acute. Base: Cordate. Margin: Doubly serrate. Texture: Fleshy, glossy and waxy; sparse pubescence on lower surface towards midvein. Petiole length: About 5.7 cm. Petiole diameter: About 7 mm. Stipules: Two per leaf; about 3 mm by 3 mm; deltoid; translucent. Color: Young foliage, upper surface: Close to 146A; iridescent. Young foliage, lower surface: Close to 148A; iridescent. Fully expanded foliage, upper surface: Dark green, close to 147A; iridescent. Fully expanded foliage, lower surface: Close to 148A; iridescent. Venation, upper surface: Close to 146A. Ventation, lower surface: Close to 146B. Petiole: Close to 147C; upper surface near base of leaf, anthocyanin, close to 53A to 53B.

Flower description:

*Flowering habit.*—Large and fully double flowers with numerous tepals arranged in axillary cymes; cyme diameter about 14.5 cm. Extremely freely flowering with usually about eight flowers per cyme, about 24 flowers per plant. Many cymes in flower simultaneously. Flowering continuous. Flowers persistent.

*Natural flowering season.*—Plants will flower year around regardless of nyctoperiod, however plants flower earlier and more abundantly from mid-February until November in the Northern Hemisphere.

*Flower longevity.*—Very long-lasting, flowers last about three weeks on the plant. Flowers do not abscise under low light conditions; excellent post-production longevity.

*Flowers.*—Aspect: Upright to outwardly facing. Shape: Rounded to oblong. Diameter: About 6.6 cm. Depth (height): Flat, about 9 mm. Fragrance: None detected.

*Flower buds.*—Length: About 1.3 cm. Diameter: About 1 cm. Color: 48A to 48B. Rate of flower opening: About 3 to 5 days.

*Tepals.*—Arrangement: Rosette. Quantity: Two large opposite tepals perpendicular to two slightly smaller tepals; about three whorls of interior tepals in groups of four; about 16 to 24 tepals per flower. Shape: Broadly cordate with rounded apex. Margin: Entire. Length, largest tepals: About 2.7 cm. Width, largest tepals: About 2.8 cm. Texture: Smooth, velvety. Color: When opening, upper surface: 50A; iridescent. When opening, lower surface: 50A to 50C; iridescent. Fully opened, upper surface: 50A to 47A to 47B; iridescent. Fully opened, lower surface: 47C; iridescent.

*Peduncles.*—Angle: Mostly erect. Strength: Strong but flexible. Length: About 1.4 cm. Color: 146B.

*Pedicels.*—Angle: About 30 to 45° from vertical. Strength: Strong but flexible. Length: About 1 cm. Color: 146D.

*Bracts.*—Arrangement: Two, opposite. Shape: Very broadly cordate; apex, acute. Margin: Entire. Color (Both surfaces): Light Green.

*Reproductive organs.*—Stamens: None formed. Pistils: None formed.

Disease resistance: Resistance to diseases common to Begonia has not been determined.

Seed production: Seed production has not been observed as reproductive organs are not formed.

It is claimed:

1. A new and distinct cultivar of Begonia plant named 'Dana', as illustrated and described.

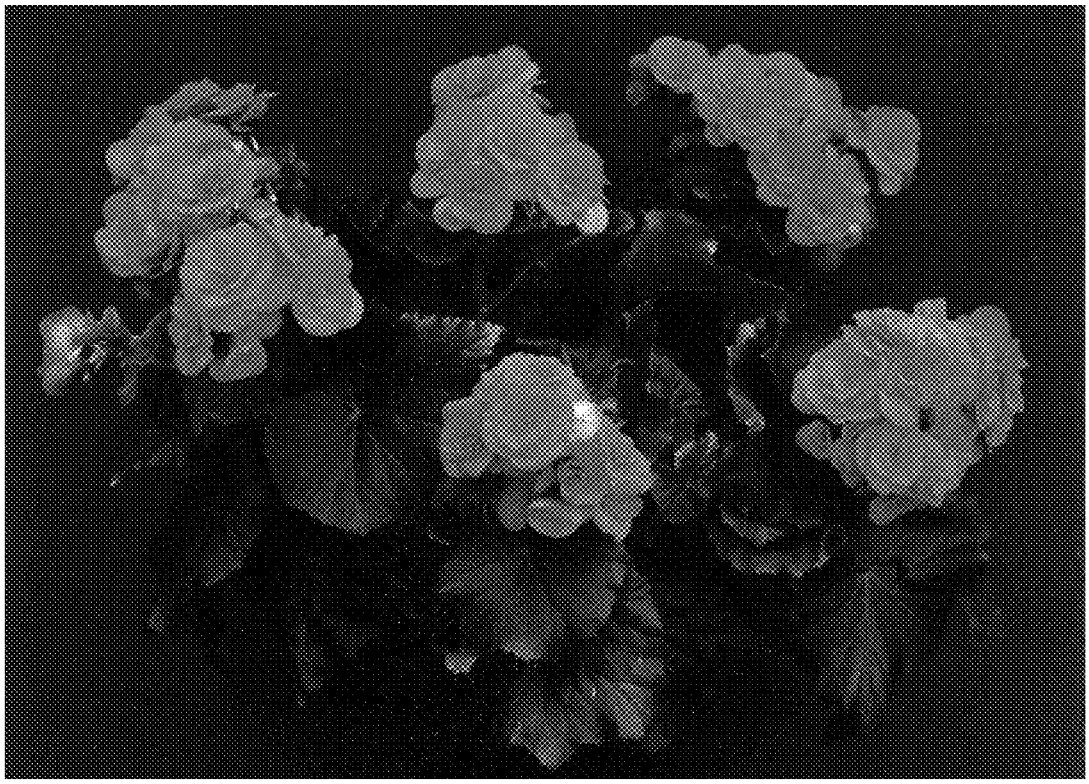
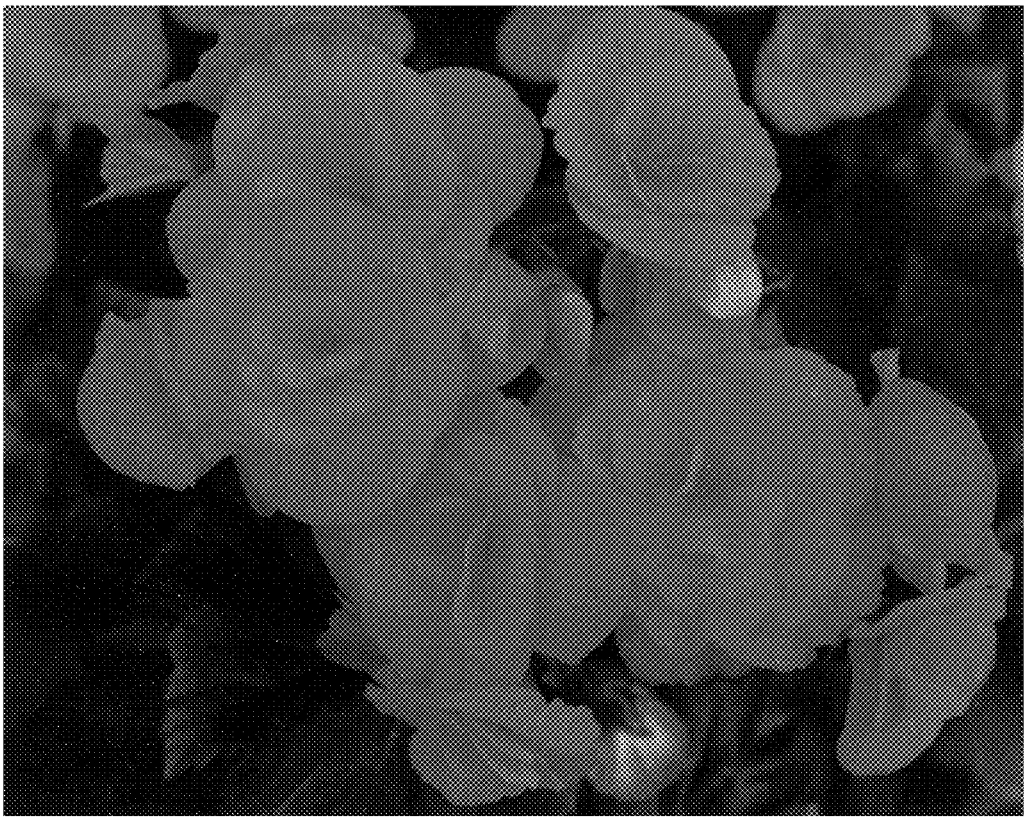

* * * * *